(12) United States Patent
Sakaguchi et al.

(10) Patent No.: US 12,333,718 B2
(45) Date of Patent: Jun. 17, 2025

(54) METHOD FOR GENERATING MODEL BY RECOGNIZING CROSS-SECTION REGIONS IN UNITS OF PIXELS

(71) Applicant: TERUMO KABUSHIKI KAISHA, Tokyo (JP)

(72) Inventors: Yuki Sakaguchi, Isehara (JP); Yusuke Seki, Tokyo (JP); Akira Iguchi, Mishima (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 344 days.

(21) Appl. No.: 17/955,810

(22) Filed: Sep. 29, 2022

(65) Prior Publication Data
US 2023/0020596 A1  Jan. 19, 2023

Related U.S. Application Data

(63) Continuation of application No. PCT/JP2021/009343, filed on Mar. 9, 2021.

(30) Foreign Application Priority Data

Mar. 30, 2020 (JP) .................................. 2020-061513

(51) Int. Cl.
*G06T 7/00* (2017.01)
*G06T 7/62* (2017.01)

(52) U.S. Cl.
CPC .............. *G06T 7/0012* (2013.01); *G06T 7/62* (2017.01); *G06T 2207/10101* (2013.01);
(Continued)

(58) Field of Classification Search
CPC ... G06T 7/0012; G06T 7/0014; G06T 7/0016; G06T 7/60; G06T 7/62;
(Continued)

(56) References Cited

U.S. PATENT DOCUMENTS 10,349,910 B2 * 7/2019 Zhong .................... A61B 5/055
11,278,259 B2 * 3/2022 Yang ..................... G06T 7/0012
(Continued)

FOREIGN PATENT DOCUMENTS

CN    106408017 A    2/2017
CN    109091167 A    12/2018
(Continued)

OTHER PUBLICATIONS

Miyagawa, Makoto, et al. "Detecting vascular bifurcation in IVOCT images using convolutional neural networks with transfer learning." IEEE Access 7, pp. 66167-66175 (Year: 2019).*
(Continued)

*Primary Examiner* — Scott A Rogers
(74) *Attorney, Agent, or Firm* — BUCHANAN INGERSOLL & ROONEY PC

(57) ABSTRACT

A computer is caused to perform processing of: acquiring a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and recognizing a main trunk cross-section, a side branch cross-section, and a bifurcated portion cross-section by inputting the acquired medical images into a learning model configured to recognize the main trunk cross-section, the side branch cross-section, and the bifurcated portion cross-section.

13 Claims, 13 Drawing Sheets

(52) U.S. Cl.
CPC ............... *G06T 2207/10132* (2013.01); *G06T 2207/20081* (2013.01); *G06T 2207/30101* (2013.01)

(58) Field of Classification Search
CPC . G06T 2207/10101; G06T 2207/10132; A61B 8/08; A61B 8/085; A61B 8/0891; A61B 8/12; A61B 8/5215; A61B 8/5223
See application file for complete search history.

(56) References Cited

U.S. PATENT DOCUMENTS

| | | |
|---|---|---|
| 2012/0083696 A1 | 4/2012 | Kitamura |
| 2015/0238121 A1 | 8/2015 | Tu et al. |
| 2015/0257850 A1 | 9/2015 | Sakamoto |
| 2017/0215838 A1* | 8/2017 | Park .................... G16H 50/30 |
| 2017/0262733 A1 | 9/2017 | Gulsun et al. |
| 2018/0247414 A1 | 8/2018 | Novikov et al. |
| 2019/0180438 A1 | 6/2019 | Buckler et al. |
| 2021/0312636 A1 | 10/2021 | Tu et al. |
| 2023/0017334 A1* | 1/2023 | Sakaguchi ........... G06V 10/764 |
| 2023/0222655 A1* | 7/2023 | Kusu ....................... A61B 8/12 382/128 |
| 2023/0230231 A1* | 7/2023 | Tu ......................... G06V 10/774 382/130 |
| 2023/0230244 A1* | 7/2023 | Kusu .................. G06V 10/7796 382/128 |
| 2024/0013385 A1* | 1/2024 | Tominaga ............. G06T 7/0012 |
| 2024/0013386 A1* | 1/2024 | Sakaguchi ............. G06V 40/14 |
| 2024/0070855 A1* | 2/2024 | Mao ...................... G06T 7/0012 |

FOREIGN PATENT DOCUMENTS

| | | |
|---|---|---|
| JP | 2012075702 A | 4/2012 |
| JP | 2019165970 A | 10/2019 |
| WO | 2015136853 A1 | 9/2015 |
| WO | 2020/006853 A1 | 1/2020 |

OTHER PUBLICATIONS

Porto, C. D. N., et al. "Classification of bifurcations regions in IVOCT images using support vector machine and artificial neural network models." Medical Imaging 2017: Computer-Aided Diagnosis. vol. 10134. SPIE (Year: 2017).*

International Search Report (PCT/ISA/210) with translation and Written Opinion (PCT/ISA/237) mailed on May 11, 2021, by the Japan Patent Office as the International Searching Authority for International Application No. PCT/JP2021/009343. (9 pages).

Macedo et al., "A Bifurcation Identifier for IV-OCT using Orthogonal Least Squares and Supervised Machine Learning", Computerized Medical Imaging and Graphics, (Sep. 21, 2015), vol. 46, pp. 237-248.

The extended European Search Report issued Jul. 27, 2023, by the European Patent Office in corresponding European Patent Application No. 21781271.8-1126. (8 pages).

The First Office Action issued on Sep. 20, 2024, by the State Intellectual Property Office of the People's Republic of China in corresponding Chinese Patent Application No. 202180024534.6 and an English translation of the Action. (13 pages).

English translation of the Office Action (Notice of Reasons for Refusal) issued on Jun. 4, 2024, in corresponding Japanese Patent Application No. 2022-511734. (3 pages).

* cited by examiner

[FIG. 1]
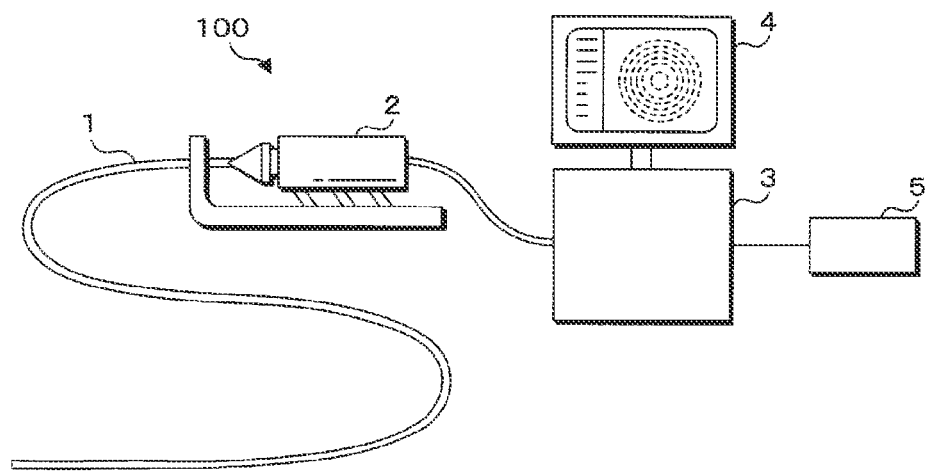
[FIG. 2]
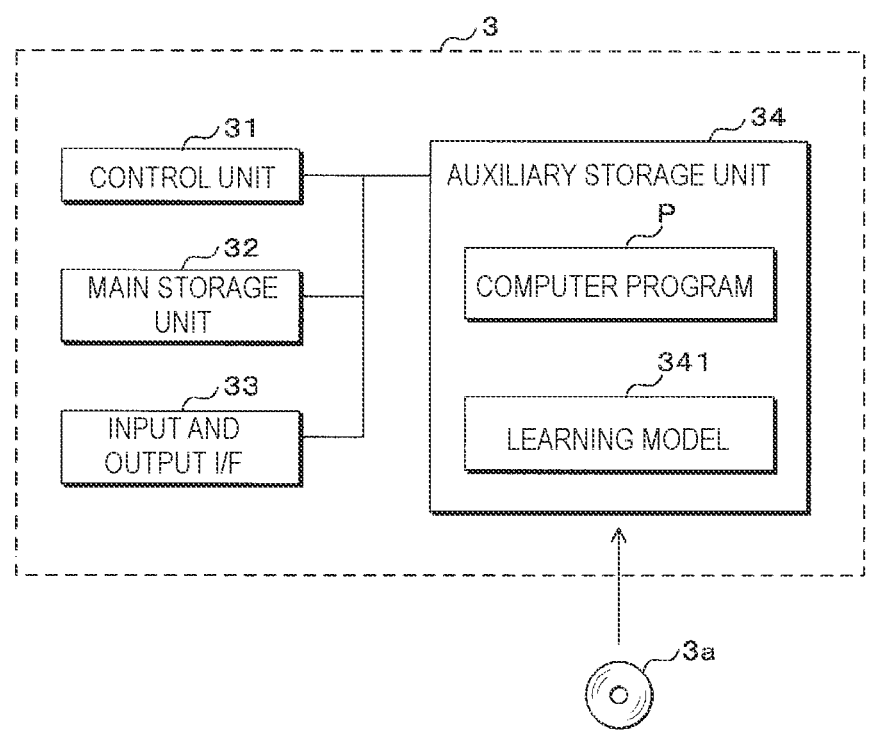

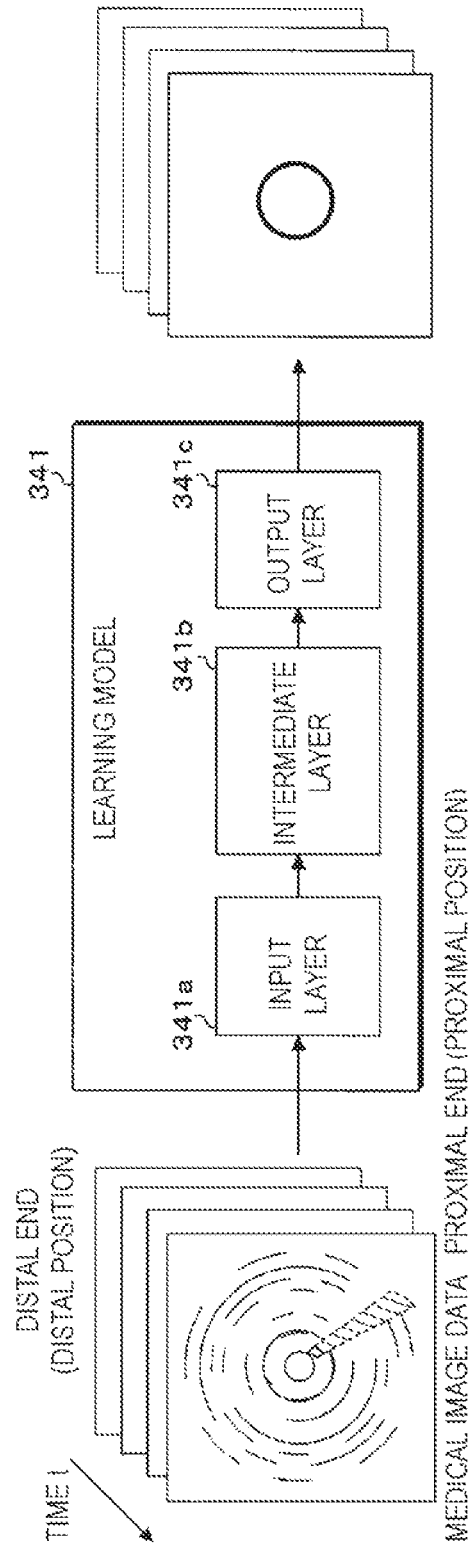
[FIG. 3]

[FIG. 4]
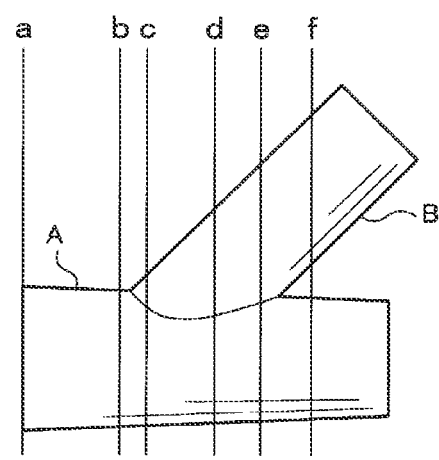

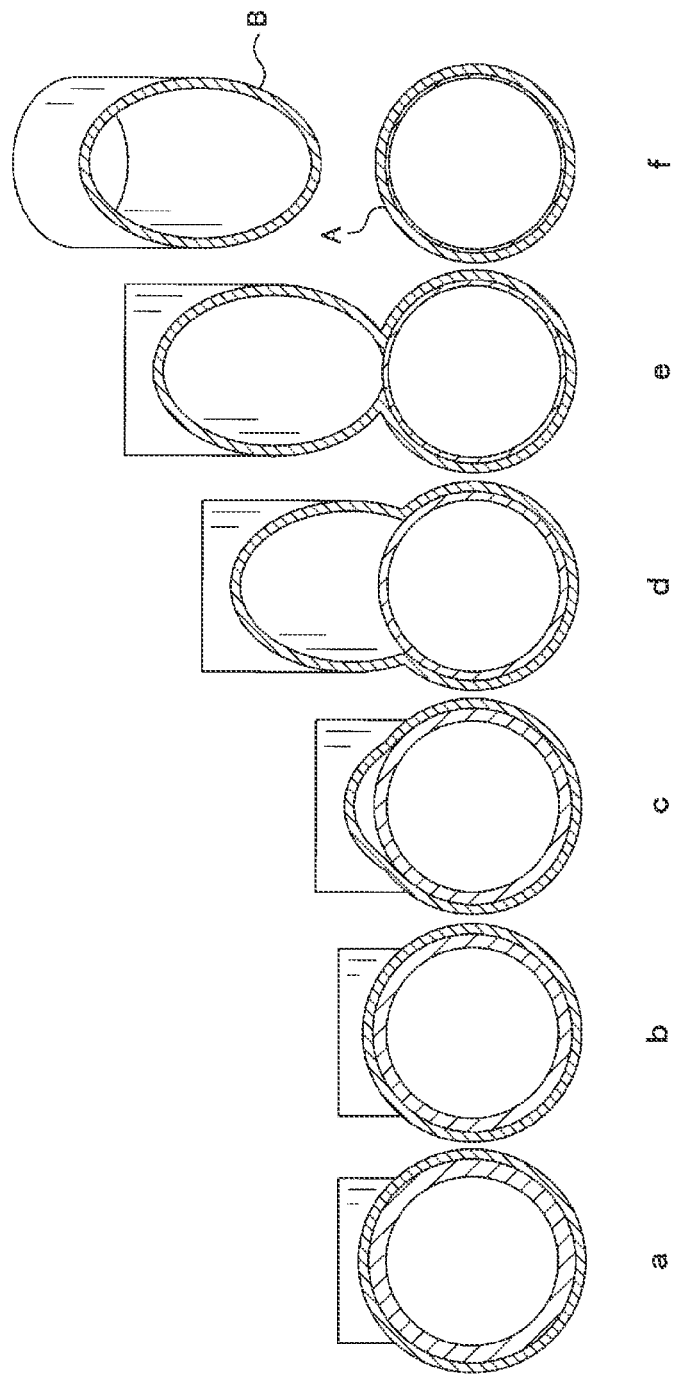

[FIG. 6]
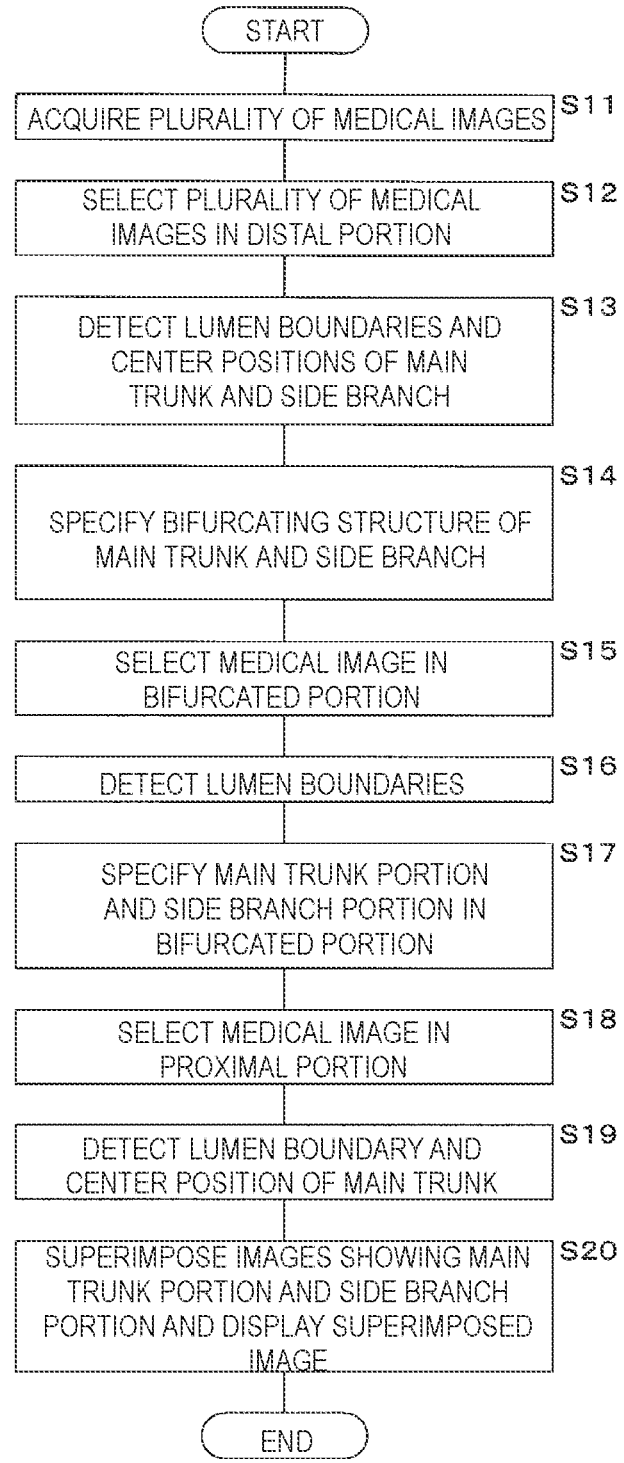

[FIG. 7]
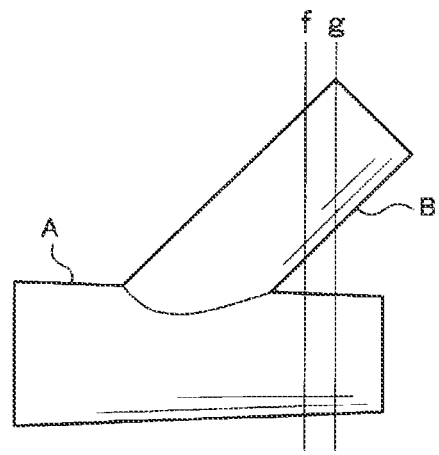
[FIG. 8]
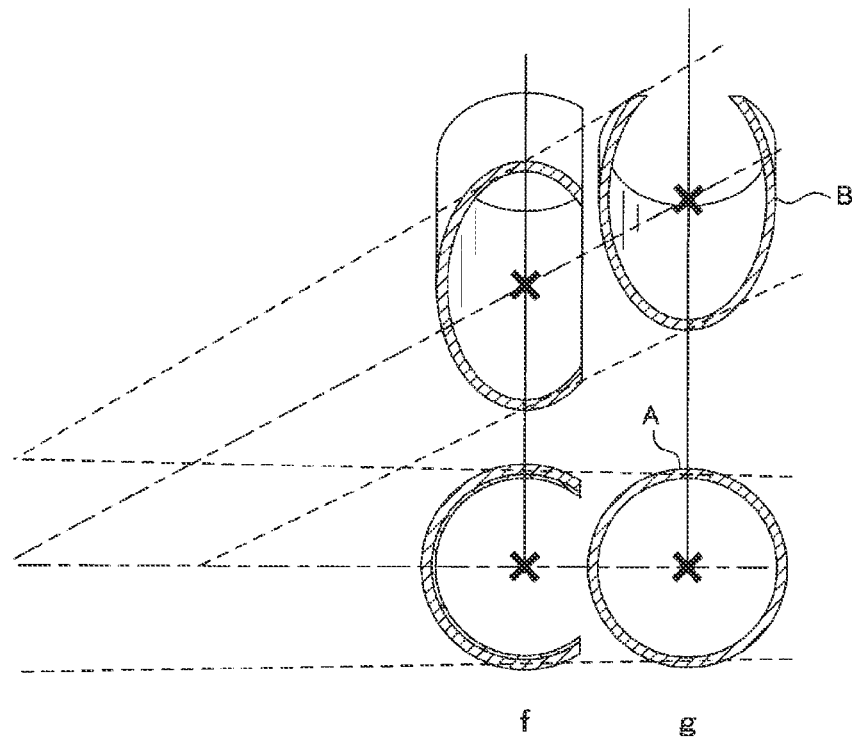

[FIG. 9]
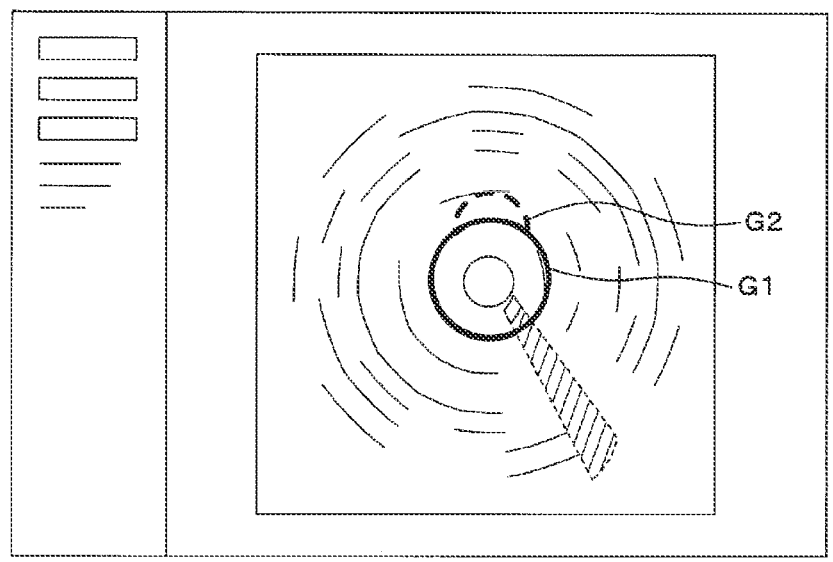

[FIG. 10]
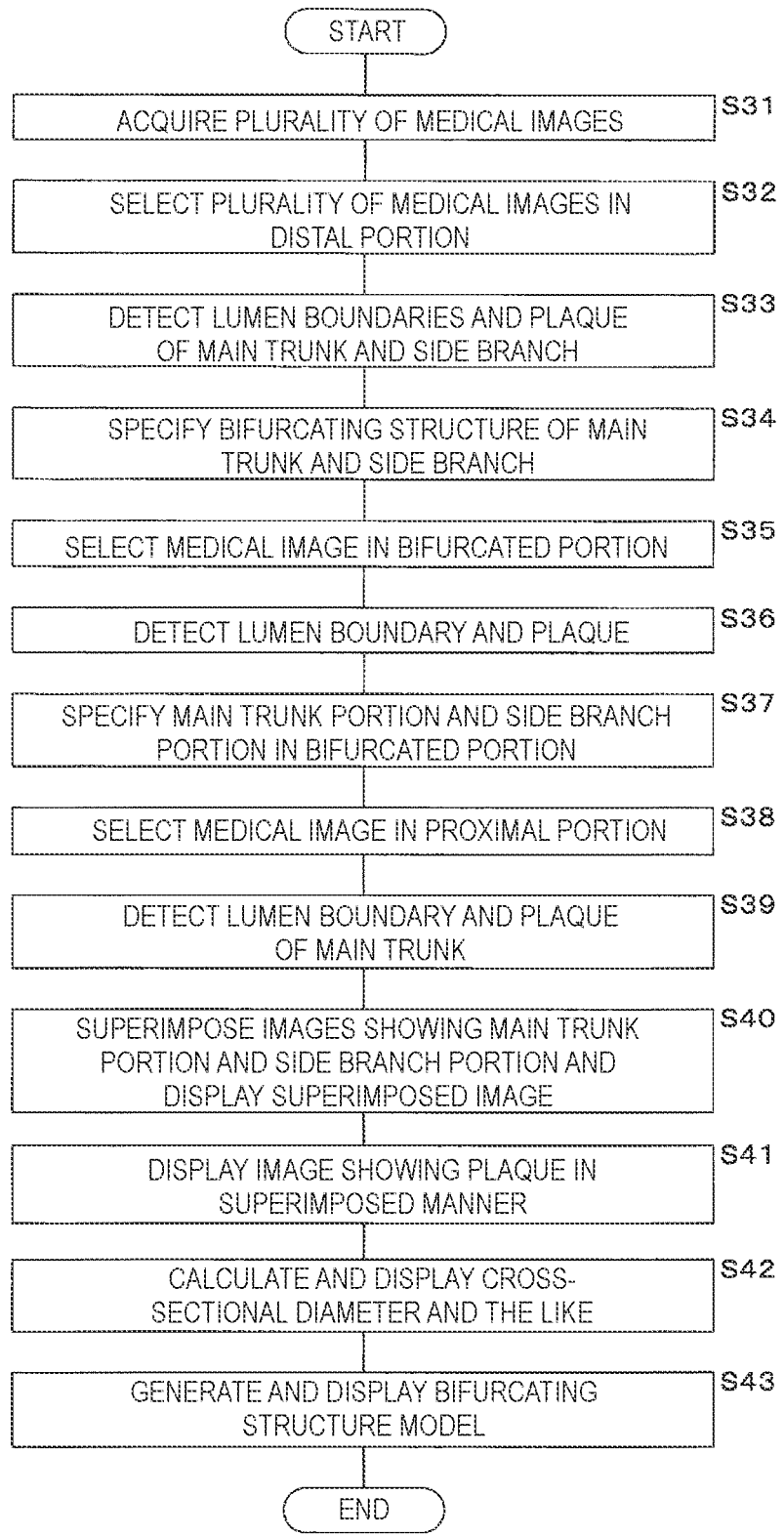

[FIG. 11A]
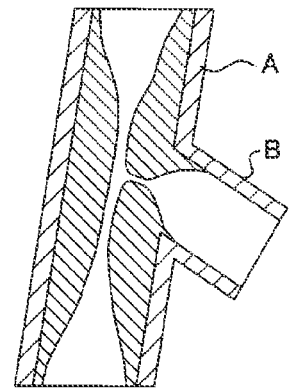
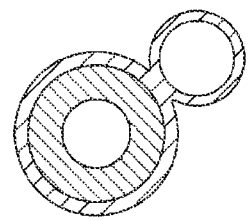
[FIG. 11B]
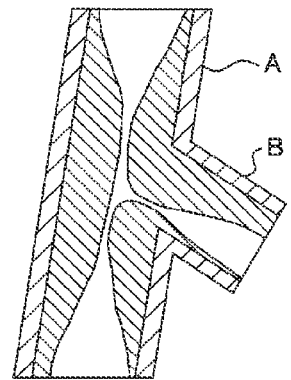
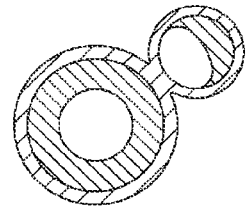

[FIG. 11C]
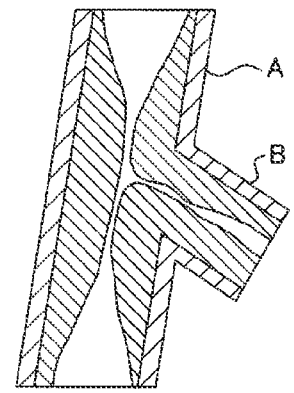
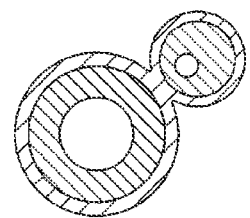

[FIG. 12]
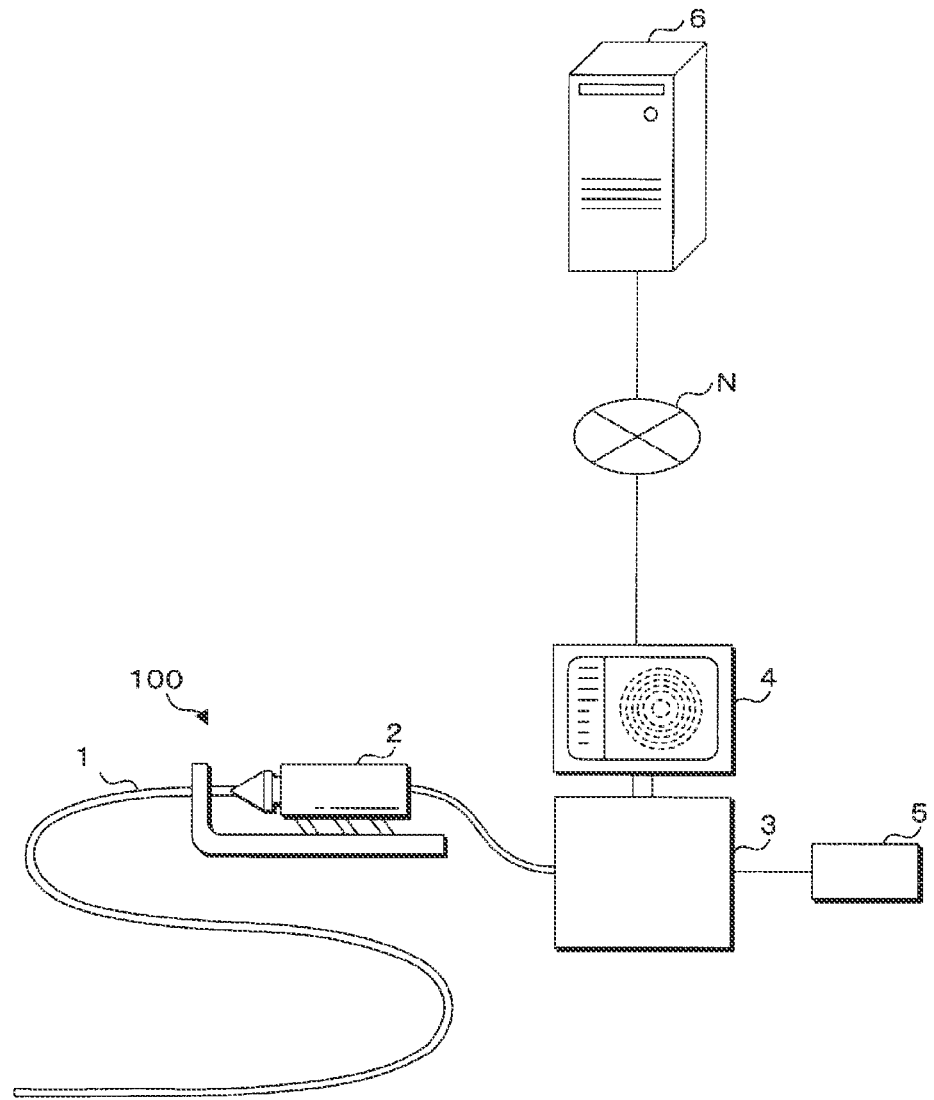

[FIG. 13]
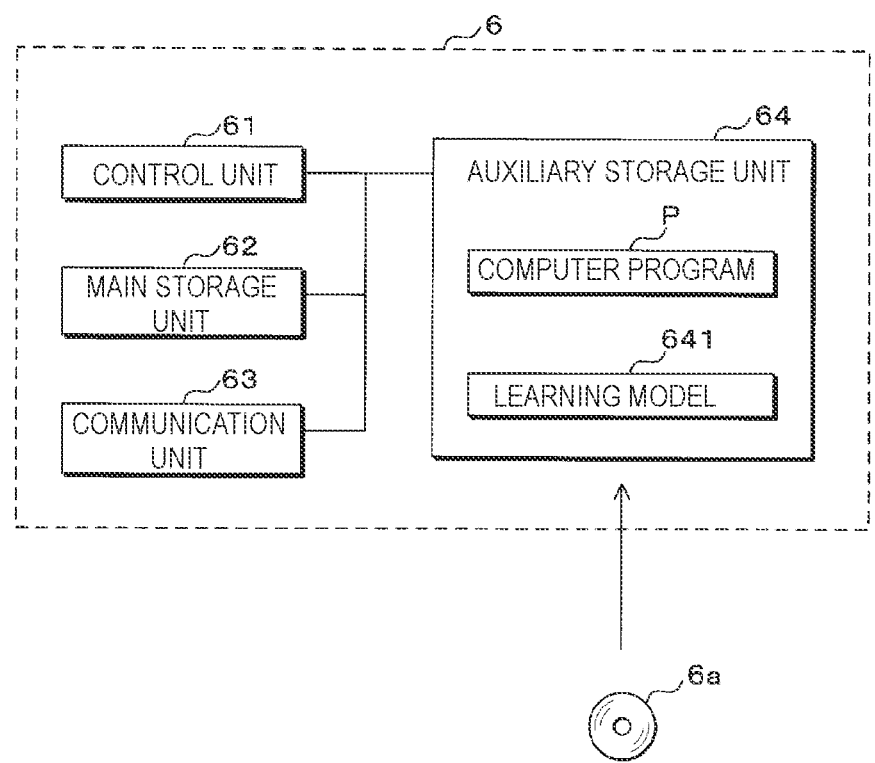

[FIG. 14]
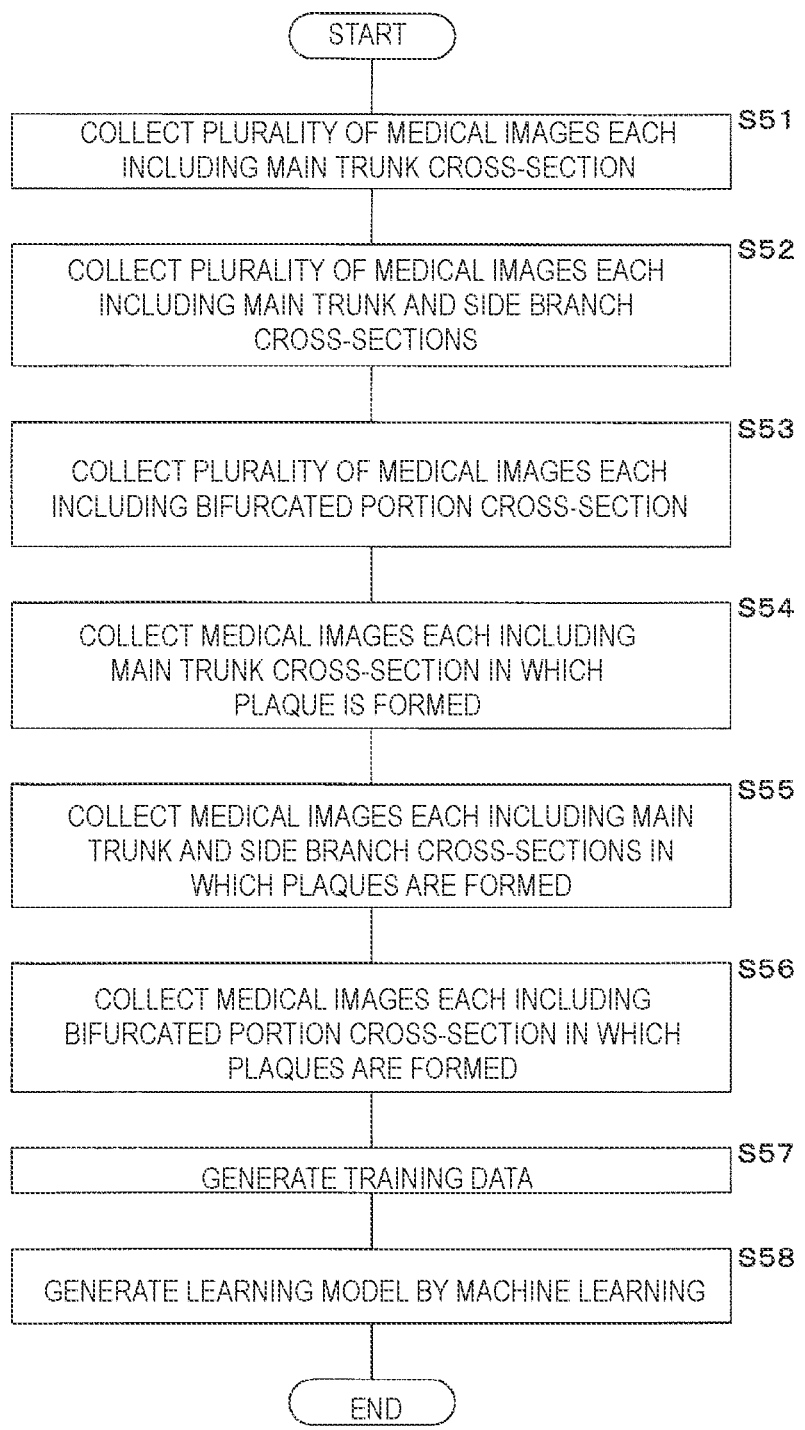

METHOD FOR GENERATING MODEL BY RECOGNIZING CROSS-SECTION REGIONS IN UNITS OF PIXELS

CROSS-REFERENCES TO RELATED APPLICATIONS

This application is a continuation of International Application No. PCT/JP2021/009343 filed on Mar. 9, 2021, and claims the benefit of Japanese Application No. JP2020-061513 filed on Mar. 30, 2020, the entire content of each of which is incorporated herein by reference.

TECHNOLOGICAL FIELD

The present disclosure relates to a computer program, an information processing method, an information processing device, and a method for generating a model.

BACKGROUND DISCUSSION

In intra vascular ultrasound (IVUS) methods, an intravascular diagnosis catheter moves an ultrasound sensor from a distal position to a proximal position of a blood vessel, and scans the blood vessel and surrounding tissues thereof. The generated medical image including an ultrasound tomographic image of the blood vessel is used for ultrasonic examination inside the blood vessel.

Meanwhile, for a purpose of assisting a doctor to perform diagnosis, a technique of adding information to the medical image by image processing or machine learning is developed.

CITATION LIST

Patent Literature

PTL 1: JP-A-2019-165970

SUMMARY

Technical Problem

However, there is a problem in that it is difficult to recognize an image of a lumen boundary of a bifurcated portion of the blood vessel in one tomographic image and discriminate between a main trunk and a side branch of the blood vessel, and useful information cannot be added to the medical image.

An object of the present disclosure is to provide a computer program, an information processing method, an information processing device, and a method for generating a model capable of analyzing a medical image obtained by scanning a lumen organ, and recognizing a main trunk and a side branch of a blood vessel.

Solution to Problem

A computer program according to the present disclosure causes a computer to perform processing of: acquiring a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and recognizing a main trunk cross-section, a side branch cross-section, and a bifurcated portion cross-section by inputting the acquired medical images into a learning model configured to recognize the main trunk cross-section, the side branch cross-section, and the bifurcated portion cross-section.

An information processing method according to the present disclosure includes a computer performing processing of: acquiring a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and recognizing a main trunk cross-section, a side branch cross-section, and a bifurcated portion cross-section by inputting the acquired medical images into a learning model configured to recognize the main trunk cross-section, the side branch cross-section, and the bifurcated portion cross-section.

An information processing device according to the present disclosure includes: an acquisition unit configured to acquire a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and a learning model configured to recognize, when the acquired medical images are input, a main trunk cross-section, a side branch cross-section, and a bifurcated portion cross-section, and output information indicating the main trunk cross-section, the side branch cross-section, and the bifurcated portion cross-section.

A method for generating a model according to the present disclosure includes performing the following processing in a computer: generating training data in which data indicating a lumen cross-section is attached to a plurality of medical images each including a main trunk cross-section, a plurality of medical images each including the main trunk cross-section and a side branch cross-section, and a plurality of medical images each including a bifurcated portion cross-section that are generated based on signals detected by a catheter inserted into a lumen organ while the catheter is moving a sensor along a longitudinal direction of a lumen organ, the lumen organ including a main trunk, a side branch branched from the main trunk, and a bifurcated portion of the main trunk and the side branch; and generating, based on the generated training data, a learning model configured to recognize the main trunk cross-section, the side branch cross-section, and the bifurcated portion cross-section when the medical images are input.

Advantageous Effect of Invention

According to the present disclosure, a medical image obtained by scanning a lumen organ can be analyzed and a main trunk and a side branch of a blood vessel can be recognized.

BRIEF DESCRIPTION OF THE DRAWINGS

FIG. 1 is an explanatory diagram showing a configuration example of a diagnostic imaging apparatus.

FIG. 2 is a block diagram showing a configuration example of an image processing device.

FIG. 3 is an explanatory diagram showing an image recognition method using a learning model.

FIG. 4 is an explanatory diagram showing a branched blood vessel.

FIG. 5 is an explanatory diagram showing tomographic images of the blood vessel obtained by scanning the branched blood vessel.

FIG. 6 is a flowchart showing a procedure of an information processing method according to a first embodiment.

FIG. 7 is a side view of a blood vessel showing a method for specifying a bifurcating structure of the blood vessel.

FIG. 8 is a cross-sectional view of the blood vessel showing the method for specifying the bifurcating structure of the blood vessel.

FIG. 9 is an explanatory diagram showing a display example of guide images.

FIG. 10 is a flowchart showing a procedure of an information processing method according to a second embodiment.

FIG. 11A is an explanatory diagram showing model images of a main trunk and a side branch.

FIG. 11B is an explanatory diagram showing model images of the main trunk and the side branch.

FIG. 11C is an explanatory diagram showing model images of the main trunk and the side branch.

FIG. 12 is an explanatory diagram showing a configuration example of a diagnostic imaging system.

FIG. 13 is a block diagram showing a configuration example of an information processing device.

FIG. 14 is a flowchart showing a method for generating a learning model.

DETAILED DESCRIPTION

Specific examples of a computer program, an information processing method, an information processing device, and a method for generating a model according to embodiments of the invention will be described below with reference to the drawings.

First Embodiment

FIG. 1 is an explanatory diagram showing a configuration example of a diagnostic imaging apparatus 100. The diagnostic imaging apparatus 100 is an apparatus for generating a medical image including an ultrasound tomographic image of a blood vessel (lumen organ) by an intra vascular ultra sound (IVUS) method, and performing an ultrasound examination and diagnosis inside the blood vessel. In particular, the diagnostic imaging apparatus 100 according to the first embodiment is an apparatus that analyzes a bifurcating structure of the blood vessel to discriminate between a main trunk A and a side branch B branched from the main trunk A, and superimposes and displays guide images G1 and G2 (see FIG. 9) showing the bifurcating structure on the medical image.

The diagnostic imaging apparatus 100 includes a catheter 1, a motor drive unit (MDU) 2, an image processing device (information processing device) 3, a display device 4, and an input device 5. The diagnostic imaging apparatus 100 generates the medical image including the ultrasound tomographic image of the blood vessel by the IVUS method using the catheter 1, and performs the ultrasound examination inside the blood vessel.

The catheter 1 is a diagnostic imaging catheter for obtaining the ultrasound tomographic image of the blood vessel by the IVUS method. The catheter 1 includes, at a distal end portion thereof, an ultrasound probe for obtaining the ultrasound tomographic image of the blood vessel. The ultrasound probe includes an ultrasound transducer that emits an ultrasound in the blood vessel, and an ultrasound sensor that receives a reflected wave (ultrasound echo) reflected by a biological tissue of the blood vessel or a medical equipment. The ultrasound probe is configured to move forward and backward in a longitudinal direction of the blood vessel while rotating in a circumferential direction of the blood vessel.

The MDU 2 is a drive apparatus to which the catheter 1 is detachably attached, and controls, by driving a built-in motor according to an operation of a health care worker, an operation of the catheter 1 inserted into the blood vessel. The MDU 2 rotates the ultrasound probe of the catheter 1 in the circumferential direction while moving the ultrasound probe from a distal end (distal position) side to a proximal end (proximal position) side (see FIG. 3). The ultrasound probe continuously scans the inside of the blood vessel at a predetermined time interval, and outputs reflected wave data of a detected ultrasound to the image processing device 3.

The image processing device 3 generates, in an chronological order, a plurality of medical images including the tomographic image of the blood vessel based on the reflected wave data output from the ultrasound probe of the catheter 1 (see FIG. 3). Since the ultrasound probe scans the inside of the blood vessel while moving from the distal end (distal position) side to the proximal end (proximal position) side in the blood vessel, the plurality of medical images in the chronological order are tomographic images of the blood vessel observed at a plurality of locations from the distal position to the proximal position.

The display device 4 is a liquid crystal display panel, an organic EL display panel, or the like, and displays the medical image generated by the image processing device 3.

The input device 5 is an input interface such as a keyboard or a mouse that receives an input of various setting values when an inspection is performed, an operation on the image processing device 3, and the like. The input device 5 may be a touch panel, a soft key, a hard key, or the like provided in the display device 4.

FIG. 2 is a block diagram showing a configuration example of the image processing device 3. The image processing device 3 is a computer, and includes a control unit 31, a main storage unit 32, an input and output I/F 33, and an auxiliary storage unit 34.

The control unit 31 is implemented by using an arithmetic processing device, i.e., a processor, such as one or more central processing units (CPUs), micro-processing units (MPUs), graphics processing units (GPUs), general-purpose computing on graphics processing units (GPGPUs), tensor processing units (TPUs), or the like.

The main storage unit 32 is a temporary storage area such as a static random access memory (SRAM), a dynamic random access memory (DRAM), or a flash memory, and temporarily stores data necessary for the control unit 31 to perform arithmetic processing.

The input and output I/F 33 is an interface through which the catheter 1, the display device 4, and the input device 5 are connected. The control unit 31 acquires the reflected wave data output from the ultrasound probe via the input and output I/F 33. The control unit 31 outputs a medical image signal to the display device 4 via the input and output I/F 33. Further, the control unit 31 receives, via the input and output I/F 33, information input to the input device 5.

The auxiliary storage unit 34 is a non-transitory computer-readable storage medium, e.g., a storage device such as a hard disk, an electrically erasable programmable ROM (EEPROM), or a flash memory. The auxiliary storage unit 34 stores a computer program P performed by the control unit 31 and various types of data required for processing of the control unit 31. In addition, the auxiliary storage unit 34 stores a learning model 341.

The learning model 341 is a model that recognizes a predetermined object included in the medical image. For example, the learning model 341 can classify an object in units of pixels by using an image recognition technique using semantic segmentation, and can recognize a lumen boundary of a blood vessel included in the medical image.

The auxiliary storage unit 34 may be an external storage device connected to the image processing device 3. The computer program P may be written in the auxiliary storage unit 34 at a stage of manufacturing the image processing device 3, or the image processing device 3 may acquire the computer program P, which is distributed by a remote server apparatus, through communication and store the computer program P in the auxiliary storage unit 34. The computer program P may be in a state of being recorded readably in a non-transitory computer-readable storage and recording medium 3a such as a magnetic disk, an optical disk, or a semiconductor memory.

The control unit 31 reads and performs the computer program P stored in the auxiliary storage unit 34 or the medium 3a to acquire the medical image generated by the diagnostic imaging apparatus 100 and perform processing of detecting the lumen boundary of the blood vessel included in the medical image. Specifically, the control unit 31 detects an image region of the lumen boundary in the medical image using the learning model 341. In particular, the control unit 31 according to the first embodiment has a function of discriminating between the main trunk A and the side branch B at a bifurcated portion of the blood vessel. Then, the image processing device 3 outputs a recognition result of the lumen boundary to the diagnostic imaging apparatus 100, and displays the guide images G1 and G2 (see FIG. 9) indicating positions and regions of the main trunk A and the side branch B in order to enable the health care worker to easily recognize the lumen boundaries of the main trunk A and the side branch B which are results.

FIG. 3 is an explanatory diagram showing an image recognition method using the learning model 341. The learning model 341 is trained such that the region of the lumen boundary of the blood vessel in the medical image can be recognized in units of pixels.

The learning model 341 is, for example, a convolutional neural network (CNN) that is trained by deep learning. The learning model 341 recognizes an object in units of pixels by an image recognition technique using so-called semantic segmentation.

The learning model 341 includes an input layer 341a which receives the medical image, an intermediate layer 341b that extracts and restores feature data of the image, and an output layer 341c that outputs a label image showing the object included in the medical image in units of pixels. The learning model 341 is, for example, U-Net.

The input layer 341a of the learning model 341 includes a plurality of neurons that receive an input of a pixel value of a pixel included in the medical image, and transmits the received pixel value to the intermediate layer 341b. The intermediate layer 341b includes a convolutional layer (CONV layer) and a deconvolutional layer (DECONV layer). The convolutional layer is a layer that performs dimensional compression on image data. The feature data of the object is extracted by the dimensional compression. The deconvolutional layer performs deconvolution processing to reconstruct to an original dimension. By the reconstruction processing in the deconvolutional layer, a binarized label image indicating whether the pixels in the image are an object is generated. The output layer 341c includes one or more neurons that output the label image. The label image is, for example, an image in which pixels corresponding to the lumen boundary of the blood vessel are of class "1" and pixels corresponding to the other images are of class "0".

The learning model 341 can be generated by preparing training data including a medical image including the main trunk A, a label image showing pixels and a center position of a lumen boundary of the main trunk A in the medical image, a medical image including the main trunk A and the side branch B which are completely separated from each other, a label image showing pixels and center positions of the lumen boundaries of the main trunk A and the side branch B in the medical image, a medical image including the bifurcated portion of the main trunk A and the side branch B, and a label image showing pixels of a lumen boundary of the bifurcated portion in the medical image, and performing machine learning on an untrained neural network using the training data. In the medical image including the bifurcated portion, a main trunk cross-section and a side branch cross-section are combined to each other.

As shown in FIG. 3, according to the learning model 341 trained in this way, a label image showing a region of the lumen boundary of the main trunk A in units of pixels is obtained by inputting the medical image including the main trunk A into the learning model 341. A label image showing regions of the main trunk A and the side branch B in units of pixels is obtained in the learning model 341 by inputting the medical image including both the main trunk A and the side branch B into the learning model 341. Further, a label image showing a region of the bifurcated portion in units of pixels is obtained in the learning model 341 by inputting the medical image including the bifurcated portion of the main trunk A and the side branch B into the learning model 341. In the label images obtained here, the main trunk A and the side branch B are output without being discriminated.

FIG. 4 is an explanatory diagram showing a branched blood vessel, and FIG. 5 is an explanatory diagram showing tomographic images of the blood vessel obtained by scanning the branched blood vessel. The tomographic images on planes denoted by reference numerals a to f in FIG. 4 are as shown in FIG. 5. When the main trunk A and the side branch B branched from the main trunk A are completely separated from each other (a cross-section indicated by the reference numeral f), the main trunk A and the side branch B in the medical image can be easily understood. However, in the bifurcated portion of the blood vessel (cross-sections indicated by the reference numerals c, d, and e), structures of the main trunk A and the side branch B cannot be easily understood.

The image processing device 3 according to the first embodiment performs processing of recognizing the structures of the main trunk A and the side branch B in the bifurcated portion and displaying the guide images G1 and G2 for supporting the health care worker to recognize the bifurcating structure.

FIG. 6 is a flowchart showing a procedure of the information processing method, FIG. 7 is a side view of the blood vessel showing a method for specifying the bifurcating structure of the blood vessel, and FIG. 8 is a cross-sectional view of the blood vessel showing the method for specifying the bifurcating structure of the blood vessel.

The control unit 31 acquires the plurality of medical images in the chronological order from the diagnostic imaging apparatus 100 (step S11). The plurality of medical images in the chronological order acquired here are, for example, images of the tomographic images observed from the distal position to the proximal position of the blood vessel.

The control unit 31 selects a plurality of medical images in a distal portion (step S12). The control unit 31 may select at least two medical images each including the main trunk A and the side branch B that are completely separated from each other. For example, as shown in FIG. 7, the control unit 31 may select a medical image on a cutting plane f and a medical image on a cutting plane g.

Then, the control unit 31 detects the lumen boundaries and the center positions of the main trunk A and the side branch B included in the medical image by inputting the medical images selected in step S12 into the learning model 341 (step S13).

Next, the control unit 31 specifies the bifurcating structure of the blood vessel based on a detection result of step S13 as shown in FIG. 8 (step S14). A time difference in capturing the two images selected in step S12 corresponds to a length of the main trunk A in the longitudinal direction. Specifically, a product of a moving speed of the ultrasound probe during blood vessel scanning and the time difference corresponds to a length between locations at which the two medical images are captured. In FIG. 8, a straight line (broken line) passing through centers of the main trunks A included in the two medical images indicates a center line of the main trunk A. A straight line (broken line) passing through centers of the side branches B included in the two medical images indicates a center line of the side branch B.

When center coordinates of the main trunk A imaged at a scanning time point t1 are (x1, y1) and center coordinates of the main trunk A imaged at a scanning time point $t2=t+\Delta t$ are (x2, y2), center coordinates (xN, yN) of the main trunk A at the bifurcated portion imaged at a scanning time point $tN=t+N\Delta t$ are expressed by the following equations (1) and (2).

$$xN=x1+(x2-x1)\times N \quad (1)$$

$$yN=y1+(y2-y1)\times N \quad (2)$$

When a diameter of the main trunk A imaged at the scanning time point t1 is r1 and a diameter of the main trunk A imaged at the scanning time point $t2=t+\Delta t$ is r2, a center coordinate rN of the main trunk A at the bifurcated portion imaged at the scanning time point $tN=t+N\Delta t$ is expressed by the following equation (3).

$$rN=r1+(r2-r1)\times N \quad (3)$$

The above equation (3) describes one diameter, and a long diameter and a short diameter of the main trunk A can be calculated in the same way.

Although an example in which the above equations (1) to (3) are used to estimate the center position and the diameter of the blood vessel in the bifurcated portion by linear interpolation based on the center positions and the diameters of the main trunk obtained from the two medical images has been described, the center position and the diameter of the blood vessel in another medical image may be calculated by polynomial interpolation based on the center positions of the blood vessel in three or more medical images.

Similarly, the diameter of the lumen boundary of the main trunk A may be estimated. In addition, the center position and the diameter of the side branch B in the medical image can also be calculated by the same method.

The control unit 31 specifies a region in which straight lines indicating the lumen boundary of the main trunk A and straight lines indicating the lumen boundary of the side branch B intersect with each other as the bifurcated portion.

The control unit 31 that finishes the processing of step S14 selects the medical image in the bifurcated portion (step S15), and detects the lumen boundaries of the main trunk A and the side branch B included in the medical image (step S16). The region of the lumen boundary of the main trunk A and the region of the lumen boundary of the side branch B in the bifurcated portion are recognized as regions that are partially combined.

Then, the control unit 31 specifies, based on information indicating the structure of the bifurcated portion specified in step S14, a main trunk A portion and a side branch B portion in the regions of the lumen boundaries detected in step S16 (step S17). The center position and the diameter of the main trunk A in the medical image of the bifurcated portion can be obtained based on the information on the structure of the bifurcated portion specified in step S14. That is, the control unit 31 can obtain an elliptical line indicating the main trunk A in the medical image. The control unit 31 can recognize, as the lumen boundary of the main trunk A, a region in the vicinity of the elliptical line of the main trunk A obtained based on the information on the structure of the bifurcated portion in the lumen boundary detected in step S16. Similarly, the control unit 31 can recognize, as the lumen boundary of the side branch B, a region in the vicinity of an elliptical line of the side branch B obtained based on the information on the structure of the bifurcated portion in the lumen boundary detected in step S16.

Next, the control unit 31 selects the medical image in the proximal portion which is proximal of the bifurcated portion (step S18). If the number of branches is one, only the main trunk A is included in the medical image selected in step S18. The control unit 31 detects the lumen boundary and the center position of the main trunk A included in the medical image in the proximal portion (step S19).

Then, the control unit 31 superimposes the guide images G1 and G2 indicating the main trunk A portion and the side branch B portion in the medical image onto the medical image, and displays the superimposed image (step S20).

FIG. 9 is an explanatory diagram showing a display example of the guide images G1 and G2. In the medical image of the bifurcated portion, as shown in FIG. 9, cross-sections of the main trunk A and the side branch B are partially combined, and it is difficult to clearly discriminate between the lumen boundary of the main trunk A portion and the lumen boundary of the side branch B portion. Therefore, the control unit 31 superimposes the guide image G1 corresponding to the region of the lumen boundary of the main trunk A onto the medical image and displays the superimposed image. The guide image G1 is an image having substantially the same shape as the region of the lumen boundary of the main trunk A.

Further, the control unit 31 superimposes the guide image G2 corresponding to the region of the lumen boundary of the side branch B onto the medical image and displays the superimposed image. The guide image G2 is an image having substantially the same shape as the region of the lumen boundary of the side branch B.

The control unit 31 may display the guide images G1 and G2 in different modes for the guide image G1 and the guide image G2. For example, the guide images G1 and G2 having different line types and colors may be displayed. An original image on which the guide images G1 and G2 are not superimposed may be displayed adjacently with an image obtained by superimposing the guide images G1 and G2 onto the medical image. Further, the image on which the guide images G1 and G2 are superimposed and the original image on which the guide images G1 and G2 are not superimposed may be selectively switched and displayed.

In addition, the control unit 31 may display the guide images G1 and G2 such that the lumen boundary of the main trunk A or the side branch B that does not appear in the medical image is complemented. For example, in the example shown in FIG. 9, a part of the lumen boundary that is to be annular is missing, but the lumen boundary of the main trunk A and the lumen boundary of the side branch B may be displayed by estimating the missing part.

According to the computer program P, the image processing device 3, and the information processing method configured in this way, the medical image obtained by scanning the blood vessel can be analyzed and the main trunk A and the side branch B of the blood vessel can be recognized.

In addition, the guide images G1 and G2 showing the lumen boundaries of the main trunk A and the side branch B of the blood vessel are displayed, and the health care worker can be supported to recognize the lumen boundaries of the main trunk A and the side branch B.

The image processing device 3, the computer program P, and the information processing method described in the first embodiment are examples, and are not limited to the configuration of the first embodiment.

For example, in the first embodiment, although the blood vessel is exemplified as an observation target or a diagnosis target, the invention can also be applied to a case in which a lumen organ such as a bowel other than the blood vessel is observed.

The ultrasound image has been described as an example of the medical image, and the medical image is not limited to the ultrasound image. The medical image may be, for example, an optical coherence tomography (OCT) image.

Second Embodiment

An image processing device according to a second embodiment is different from that of the first embodiment in that a lumen boundary and a plaque of the blood vessel are recognized, diameters, cross-sectional areas, volumes, and the like of the main trunk A and the side branch B can be calculated and displayed, and a model image in which a bifurcating structure is reproduced can be generated and displayed, and thus the differences will be mainly described below. Since other configurations, and operations and effects are the same as those of the first embodiment, corresponding portions are denoted by the same reference numerals and detailed descriptions are omitted.

The learning model 341 according to the second embodiment is, for example, a model that recognizes the lumen boundary and the plaque of the blood vessel included in the medical image.

FIG. 10 is a flowchart showing a procedure of an information processing method according to the second embodiment. The control unit 31 according to the second embodiment performs the same processing as that of steps S11 to S20 of the first embodiment, and detects the lumen boundary and the plaque of the blood vessel in steps S33, S36, and S39.

Next, the control unit 31 superimposes a guide image showing the plaque onto the medical image, and displays the superimposed image (step S41). A health care worker can select whether the guide image showing the plaque is necessary by using the input device 5. The control unit 31 does not display the guide image when receiving information indicating that the guide image is unnecessary, and displays the guide image when receiving information indicating that the guide image is necessary.

Next, the control unit 31 calculates the cross-sectional diameter, the cross-sectional area, or the volume per unit length of a lumen of the main trunk A, and displays, on the display device 4, the calculated cross-sectional diameter, the calculated cross-sectional area, and the calculated volume of the lumen of the main trunk A in a superimposed manner (step S42).

Similarly, the control unit 31 calculates the cross-sectional diameter, the cross-sectional area, or the volume per unit length of a lumen of the side branch B based on the bifurcating structure specified in step S34, and displays, on the display device 4, the calculated cross-sectional diameter, the calculated cross-sectional area, and the calculated volume of the lumen of the side branch B (step S42). However, as shown in FIG. 8, a tomographic image of the side branch B scanned by the catheter 1 inserted through the main trunk A is a tomographic image (hereinafter, referred to as an oblique tomographic image) obtained by obliquely cutting the side branch B. Therefore, the control unit 31 converts a cross-sectional diameter, a cross-sectional area, or a volume of a lumen of the side branch B in the oblique tomographic image into a cross-sectional diameter, a cross-sectional area, or a volume of a lumen in a tomographic image (hereinafter, referred to as an axial tomographic image) obtained by cutting the side branch B substantially perpendicularly, that is, a tomographic image obtained by cutting the side branch B along a plane substantially perpendicular to a center line of the side branch B. For example, an angle θ formed by a center line of the main trunk A and a center line of the side branch B may be calculated, the oblique tomographic image may be converted into the axial image using the angle θ, and the cross-sectional diameter, the cross-sectional area, or the volume per unit length of the lumen of the side branch B may be calculated.

Next, the control unit 31 reproduces the model image representing the bifurcating structure of the blood vessel based on the bifurcating structure calculated in step S34 and a recognition result of the lumen boundary and the plaque detected based on the medical image, and displays the reproduced model image on the display device 4 (step S43).

FIGS. 11A to 11C are explanatory diagrams showing model images of the main trunk A and the side branch B. For example, as shown in upper parts of FIGS. 11A to 11C, the control unit 31 may generate a cross section of the blood vessel as the model image. The model image shows a blood vessel wall portion, the lumen boundary, and the plaque portion of the blood vessel.

Further, as shown in lower parts of FIGS. 11A to 11C, the control unit 31 may generate cross-sectional images of the main trunk A and the side branch B as the model images. The model images also show the blood vessel wall portion, the lumen boundary, and the plaque portion of the blood vessel. Further, when generating a cross-sectional image of the side branch B, the control unit 31 may generate a model image converted into the axial image.

According to the computer program P, the image processing device 3, and the information processing method configured in this way, the guide image showing the plaque formed on the blood vessel wall can be displayed and the health care worker can be guided to recognize the plaque portion.

The cross-sectional diameters, the areas, and the volumes of the lumens of the main trunk A and the side branch B can be calculated and displayed.

The model image representing the bifurcating structure can be generated and displayed, and the health care worker can be guided to recognize the bifurcated portion of the blood vessel. In particular, by displaying the model image of the cross section displaying the lumen boundaries and plaques of the main trunk A and the side branch B, the plaque formed in the blood vessel can be recognized more easily.

Further, by displaying the axial cross-sections of the main trunk A and the side branch B, the plaque formed in the blood vessel can be recognized more easily.

Third Embodiment

FIG. 12 is an explanatory diagram showing a configuration example of a diagnostic imaging system. The diagnostic imaging system according to a third embodiment is different from that of the first embodiment in that an information processing device 6, which is a server, performs processing of analyzing a medical image, and the above difference will be mainly described later. Since other configurations and effects are the same as those of the first embodiment or the second embodiment, the corresponding portions are denoted by the same reference numerals and detailed descriptions are omitted.

The diagnostic imaging system according to the third embodiment includes the information processing device 6 and a diagnostic imaging apparatus 200. The information processing device 6 and the diagnostic imaging apparatus 200 are communicably connected to each other via a network N such as a local area network (LAN) or the Internet.

FIG. 13 is a block diagram showing a configuration example of the information processing device 6. The information processing device 6 is a computer, and includes a control unit 61, a main storage unit 62, a communication unit 63, and an auxiliary storage unit 64. The communication unit 63 is a communication circuit for performing transmission and reception of data to and from the image processing device 3 via the network N. Hardware configurations of the control unit 61, the main storage unit 62, the communication unit 63, and the auxiliary storage unit 64 are the same as those of the image processing device 3 described in the first embodiment. The computer program P, a learning model 641, and a recording medium 6a stored in the auxiliary storage unit 64 are also the same as various programs, models, and the like of the first or second embodiment. The information processing device 6 may be a multi-computer including a plurality of computers, or may be a virtual machine virtually constructed by software. The information processing device 6 may be a local server installed in the same facility (hospital or the like) as the diagnostic imaging apparatus 200, or may be a cloud server communicably connected to the diagnostic imaging apparatus 200 via the Internet or the like.

FIG. 14 is a flowchart showing a method for generating the learning model 641. The control unit 61 collects a plurality of medical images each including a main trunk cross-section (step S51). For example, the control unit 61 collects the medical images from the diagnostic imaging apparatus 200.

Next, the control unit 61 collects a plurality of medical images each including the main trunk cross-section and a side branch cross-section (step S52). Similarly, the control unit 61 collects a plurality of medical images each including a bifurcated portion cross-section (step S53).

Then, the control unit 61 collects a plurality of medical images each including the main trunk cross-section in which a plaque is formed (step S54). Then, the control unit 61 collects a plurality of medical images each including the main trunk cross-section and the side branch cross-section in which the plaques are formed (step S55). Similarly, the control unit 61 collects a plurality of medical images each including a bifurcated portion cross-section in which the plaques are formed (step S56).

Next, the control unit 61 generates training data in which label images are correlated with the medical images collected in steps S51 to S56 (step S57). A label image of the medical image including the main trunk cross-section is an image showing pixels of the lumen boundary and pixels of the plaque in the main trunk A. A label image of the medical image including the main trunk cross-section and the side branch cross-section is an image showing pixels of the lumen boundaries and pixels of the plaques in the main trunk A and the side branch B. A label image of the medical image including the bifurcated portion cross-section is an image showing pixels of the lumen boundaries and pixels of the plaques in the main trunk A and the side branch B at the bifurcated portion. A label image of the medical image including the main trunk cross-section in which the plaque is formed is an image showing pixels of the lumen boundary and pixels of the plaque in the main trunk A, and pixels of the plaque. A label image of the medical image including the main trunk cross-section and the side branch cross-section in which the plaques are formed is an image showing pixels of the lumen boundaries and pixels of the plaques in the main trunk A and the side branch B, and pixels of the plaque. A label image of the medical image including the bifurcated portion cross-section in which the plaque is formed is an image showing pixels of the lumen boundaries and pixels of the plaques in the main trunk A and the side branch B at the bifurcated portion, and pixels of the plaque.

Then, the control unit 61 generates the learning model 641 by performing machine learning on an untrained neural network using the generated training data (step S58).

According to the learning model 641 trained in this way, the label image showing a region of the lumen boundary of the main trunk A and a region of the plaque portion in units of pixels is obtained by inputting the medical image including the main trunk A into the learning model 641. The label image showing regions of the main trunk A and the side branch B and regions of the plaque portions in units of pixels is obtained in the learning model 641 by inputting the medical image including both the main trunk A and the side branch B into the learning model 641. The label image showing a region of the lumen boundaries and a region of the plaque portions at the bifurcated portion in units of pixels is obtained by inputting the medical image including bifurcated portion of the main trunk A and the side branch B into the learning model 641.

The information processing device 6 configured in this way acquires the medical images from the image processing device 3 via the network N, performs processing similar to that of the image processing device 3 according to the first embodiment based on the acquired medical images, and transmits a recognition result of an object to the image apparatus. The image processing device 3 acquires the recognition result of the object transmitted from the information processing device 6, superimposes the guide images G1 and G2 indicating the regions of the main trunk A and the side branch B of the blood vessel onto the medical image, and displays the superimposed image on the display device 4, as shown in FIG. 9.

In the information processing device 6, the computer program P, and the information processing method according to the third embodiment, similarly to the first embodiment, a medical image obtained by scanning the blood vessel can be analyzed and the main trunk A and the side branch B of the blood vessel can be recognized.

It is considered that the embodiments disclosed here are examples in all respects and are not restrictive. The scope of the invention is shown according to the claims rather than the above meaning, and is intended to include all changes within the meaning and the scope equivalent to the claims.

REFERENCE SIGNS LIST 1 catheter
2 MDU
3 image processing device
3a recording medium
4 display device
5 input device
6 information processing device
6a recording medium
31 control unit
32 main storage unit
33 input and output I/F
34 auxiliary storage unit
61 control unit
62 main storage unit
63 communication unit
64 auxiliary storage unit
341 learning model
P computer program
A main trunk
B side branch

What is claimed is:

1. A non-transitory computer-readable storage medium storing a computer program which, when executed by a computer of a diagnostic imaging apparatus, causes the computer to perform processing of:
    acquiring a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and
    recognizing, in units of pixels in the plurality of medical images, a main trunk cross-section region, a side branch cross-section region, and a bifurcated portion cross-section region by inputting the acquired medical images into a learning model configured to recognize the main trunk cross-section region, the side branch cross-section region, and the bifurcated portion cross-section region in units of pixels in the plurality of medical images.

2. The non-transitory computer-readable storage medium according to claim 1, wherein the processing further comprises:
    recognizing at least the main trunk cross-section region or the side branch cross-section region by inputting an acquired first medical image into the learning model;
    recognizing the bifurcated portion cross-section region by inputting an acquired second medical image into the learning model; and
    discriminating between a main trunk portion and a side branch portion constituting the bifurcated portion cross-section region based on a recognition result based on the first medical image.

3. The non-transitory computer-readable storage medium according to claim 2, wherein the processing further comprises:
    specifying a bifurcating structure of the main trunk and the side branch based on a recognition result based on a plurality of first medical images; and
    specifying the main trunk portion and the side branch portion included in the bifurcated portion cross-section region based on the specified bifurcating structure.

4. The non-transitory computer-readable storage medium according to claim 3,
    wherein the learning model is configured to recognize a plaque formed in the bifurcated portion, and
    the processing further comprises:
    recognizing the bifurcated portion cross-section region and the plaque by inputting the acquired second medical image into the learning model; and
    specifying a plaque portion included in the bifurcated portion cross-section region based on the bifurcating structure.

5. The non-transitory computer-readable storage medium according to claim 2, wherein the processing further comprises:
    specifying the bifurcating structure of the main trunk and the side branch based on the recognition result based on the plurality of first medical images, and calculating a cross-sectional diameter, a cross-sectional area, or a volume per unit length of the side branch.

6. The non-transitory computer-readable storage medium according to claim 2, wherein the processing further comprises:
    specifying the bifurcating structure of the main trunk and the side branch based on the recognition result based on the plurality of first medical images, and generating model images of the main trunk and the side branch.

7. The non-transitory computer-readable storage medium according to claim 1, wherein the processing further comprises:
    superimposing an image showing the main trunk portion or the side branch portion on a medical image including the bifurcated portion cross-section region.

8. The non-transitory computer-readable storage medium according to claim 1,
    wherein the lumen organ is a blood vessel, and
    the processing further comprises:
    acquiring a medical image of the blood vessel generated based on signals detected by the catheter.

9. An information processing device comprising:
    an acquisition unit configured to acquire a plurality of medical images generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and
    a learning model configured to recognize, when the acquired medical images are input, a main trunk cross-section region, a side branch cross-section region, and a bifurcated portion cross-section region in units of pixels in the plurality of medical images, and output information indicating the main trunk cross-section region, the side branch cross-section region, and the bifurcated portion cross-section region in units of pixels in the plurality of medical images.

10. The information processing device according to claim 9, wherein the learning model is further configured to:

recognize at least the main trunk cross-section region or the side branch cross-section region based on an acquired first medical image;

recognize the bifurcated portion cross-section region based on an acquired second medical image; and discriminate between a main trunk portion and a side branch portion constituting the bifurcated portion cross-section region based on a recognition result based on the first medical image.

11. The information processing device according to claim 10, wherein the learning model is further configured to:

specify a bifurcating structure of the main trunk and the side branch based on a recognition result based on a plurality of first medical images; and specify the main trunk portion and the side branch portion included in the bifurcated portion cross-section region based on the specified bifurcating structure.

12. The non-transitory computer-readable storage medium according to claim 11, wherein the learning model is further configured to:

recognize the bifurcated portion cross-section region and a plaque formed in the bifurcated portion based on the acquired second medical image; and specify a plaque portion included in the bifurcated portion cross-section region based on the bifurcating structure.

13. A method for generating a model, the method comprising performing the following processing in a computer:

generating training data in which data indicating a lumen cross-section is attached to a plurality of medical images each including a main trunk cross-section region, a plurality of medical images each including the main trunk cross-section region and a side branch cross-section region, and a plurality of medical images each including a bifurcated portion cross-section region that are generated based on signals detected by a catheter inserted into a lumen organ while the catheter is moving a sensor along a longitudinal direction of the lumen organ, the lumen organ including a main trunk, a side branch branched from the main trunk, and a bifurcated portion of the main trunk and the side branch; and generating, based on the generated training data, a learning model configured to recognize, in units of pixels in the plurality of medical images, the main trunk cross-section region, the side branch cross-section region, and the bifurcated portion cross-section region when the medical images are input.

* * * * *